United States Patent
Landberg et al.

(10) Patent No.: US 6,773,807 B2
(45) Date of Patent: Aug. 10, 2004

(54) REFLECTIVE LABELING TAPE

(75) Inventors: Cathy A. Landberg, Mays Landing, NJ (US); Billy W. McDonald, Dallas, TX (US)

(73) Assignee: McCalland Innovations, LLC, Dallas, TX (US)

( * ) Notice: Subject to any disclaimer, the term of this patent is extended or adjusted under 35 U.S.C. 154(b) by 188 days.

(21) Appl. No.: 10/208,550

(22) Filed: Jul. 30, 2002

(65) Prior Publication Data

US 2004/0023024 A1 Feb. 5, 2004

(51) Int. Cl.⁷ ............................................... B32B 33/00
(52) U.S. Cl. ..................... 428/343; 156/250; 156/252; 156/277; 156/278; 428/33; 428/40.1; 428/40.6; 428/40.8; 428/41.2; 428/41.6; 428/42.1; 428/42.2; 428/58; 428/354; 428/913.3; 428/914; 428/915; 442/149; 442/150; 442/151; 600/247; 600/248; 604/303; 604/304
(58) Field of Search ......................... 156/250, 252, 156/277, 278; 428/33, 40.1, 40.6, 40.8, 41.2, 41.6, 42.1, 42.2, 58, 343, 354, 913.3, 914; 442/149–151; 600/247, 248; 604/41, 58, 303, 304, 903

(56) References Cited

U.S. PATENT DOCUMENTS

| | | | |
|---|---|---|---|
| 4,246,307 A * | 1/1981 | Trautwein | 428/43 |
| 4,699,838 A * | 10/1987 | Gilbert | 428/201 |
| 4,745,916 A | 5/1988 | Seber | 128/858 |
| 5,213,565 A | 5/1993 | Rollband | 602/41 |
| 5,310,402 A | 5/1994 | Rollband | 602/42 |
| 5,480,647 A | 1/1996 | Tsai | 424/443 |
| 5,489,457 A * | 2/1996 | Vent | 428/40.9 |
| 5,806,525 A | 9/1998 | Pope, Jr. | 128/848 |
| 6,225,521 B1 | 5/2001 | Gueret | 602/54 |
| 6,382,126 B1 * | 5/2002 | Findley | 116/209 |
| 2001/0047144 A1 | 11/2001 | Tillotson et al. | 602/41 |
| 2001/0049485 A1 | 12/2001 | Wehde | 602/41 |
| 2002/0187294 A1 | 12/2002 | Zhou et al. | 428/40.1 |
| 2003/0211317 A1 | 11/2003 | Sheridan et al. | 428/343 |

* cited by examiner

*Primary Examiner*—Arti R. Singh
(74) *Attorney, Agent, or Firm*—Lieberman & Brandsdorfer, LLC

(57) ABSTRACT

An apparatus for conveying information and a method of using said apparatus during a medical emergency. The apparatus consists of a perforated adhesive tape with a front side and a back side. The back side includes an adhesive applied thereto to enable the tape to be affixed to a secondary surface. The front side includes borders on each side thereof. The borders are comprised of a reflective material. A middle section between the two borders includes a material with a surface adapted to receive indicia from a writing utensil. Adjacent segments of the tape are separated by perforations. During use, a writing utensil may be used to apply indicia to the middle section of a segment of the tape. The segment may be removed from an adjacent segment along the perforations, and the tape may be applied to a secondary surface.

13 Claims, 1 Drawing Sheet

REFLECTIVE LABELING TAPE

BACKGROUND OF THE INVENTION

1. Technical Field

This invention relates to an apparatus used by emergency medical personnel in treating an injured person. More specifically, the apparatus pertains to tapes capable of conveying information about the injured person.

2. Description of the Prior Art

Currently, when medical personnel treat patients at the accident site, the patient's medical information is marked on their skin. This enables medical personnel to interpret a previously identified injury. However, the are difficulties associated with this method of injury identification, including locating and reading the information in low light environments. In addition, if may be difficult to read the information placed on a patient having dark skin. Accordingly, there are limitations associated with placing indicia associated with injury identification directly on the patient's skin.

Adhesive tapes are well known in the medical community. They are widely used at both the site of injury and during care in a hospital. The prior art includes many forms of medical tape. Numerous tapes are used to secure bandages to the injured person. In addition to securing bandages, certain medical tapes themselves are used as bandages.

U.S. Patent Publication No. 2001/0049485 to Wehde discloses a roll of sterile adhesive tape for dressing wounds. The tape includes an adhesive on an underside surface and a sterilized gauze pad attached to the underside surface adjacent to the adhesive. A liner is placed over the gauze pad to enable the sterility of the gauze to be maintained. Upon application of the tape to an injured site, the gauze must be removed for the underside surface. Accordingly, the Wehde publication requires the sterility associated with the bandage to be maintained until the bandage is properly placed at the injury site.

U.S. Publication No. 2001/0047144 to Tillotson discloses a medical bandage with a luminescent material. The bandage includes a pad adapted to be placed over an injury and an adhesive adjacent to the pad. A top surface of the bandage may include a light emitting material to enable the bandage to be visible in low light environments. However, the bandage requires sterility because it is placed on an open wound. This sterilization step increases the production cost. In addition, the bandage is changed as needed making it an ineffective place to convey information. Because the bandage will not remain with the patient for the duration of treatment, the information marked on it will either need to be written onto each bandage or will be lost with a bandage change. While this bandage is suited for treating patients in low light environments, it is an expensive and inefficient means to convey information.

U.S. Pat. No. 5,213,565 to Rollband discloses a temporary bandage tape. A plurality of bandages are placed in the form of a roll and separated by perforations. In using the tape as a bandage, it needs to be packaged in a sterile manner. This requisite sterility makes bandaging tape expensive to produce. Additionally, these tapes are ill suited to low light environments as they do not include a material that enhances visibility in such environments. Accordingly, the Rollband patent requires sterility in the vicinity of the location of the bandages along the roll of tape to enable the bandages to be placed on or near openings in the skin of a patient.

There are shortcomings associated with the prior art as a means for conveying information. In general, the prior art associates the solution in the form of a bandage which requires an added expense in the manufacture product in view of the sterility requirement. Accordingly, it is desirable to provide a solution that enables the tape to function as a means of conveying information without the need for sterilizing the tape.

SUMMARY OF THE INVENTION

This invention comprises an apparatus for conveying information in an efficient and categoric manner.

In a first aspect of the invention, the apparatus is used to convey information in a medical emergency. The apparatus includes a tape with a front side and a back side. The front side of the tape has a section with a light reflective material, and a section of a material adapted to receive indicia from a writing utensil. The back side of the tape has an adhesive material. In a preferred embodiment, the front side of the tape may include a waterproof material. The tape may also include a perforation at intervals along the length of the tape. A piece of tape may be removed from an adjacent segment of tape along the perforation.

In a second aspect of the invention a method for conveying information in a medical emergency is provided. A length of tape is packaged with a light reflective material on a front side of the tape. The length of tape includes a plurality of segments with adjacent segments joined together at preformed perforations. Indicia is applied to a section of the front side of the tape. A segment is removed from the length of tape along a perforation. The removed segment is then adhered to a secondary surface.

Other features and advantages of this invention will become apparent from the following detailed description of the presently preferred embodiment of the invention, taken in conjunction with the accompanying drawings.

DESCRIPTION OF THE PREFERRED EMBODIMENT

Overview

The apparatus and method are adapted for use in a trauma situation for medical personnel to affix patient injury information directly to the patient. The apparatus includes a tape with a material that enables the medical personnel in a trauma team and future medical transfer team to identity the injury or perceived injuries in an efficient manner. The tape includes an underside surface adhesive material that is adapted to bond to the skin surface of a patient or to an article of clothing, and an exposed surface with a reflective material. An exposed surface of the tape includes a first section having a reflective material and a second section having a material adapted to receive indicia thereon to convey information pertaining to persons and objects involved in an evacuation situation. Accordingly, the apparatus provides an efficient and cost effective means of conveying patient injury information.

Technical Background

Figure 1:
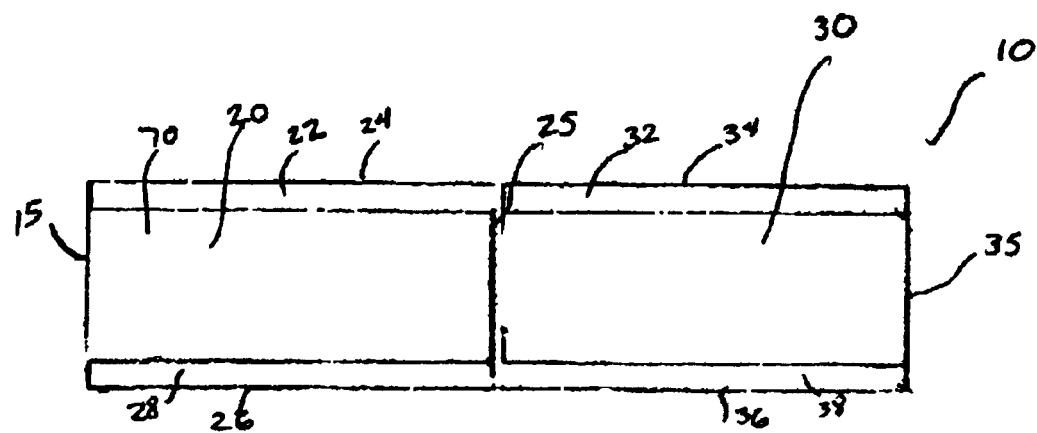
FIG. 1 is a top view of the tape according to the preferred embodiment of this invention, and is suggested for printing on the first page of the issued patent.

FIG. 1 is a top view of two adjacent segments 20 and 30 of the tape 10. The first segment 20 is connected to the second segment 30 by a plurality of perforations 25 between the two segments. A top surface of each segment of the tape 10 has three sections. A first section is a first border 22, 32 adjacent to a first edge 24, 34 of the segment. The first border 22, 32 extends along the first edge of the segment from a first set of perforations 15 to a second set of perforations 25. Similarly, the first border 32 of the second segment 30 extends from the second set of perforations 25 to a third set of perforations 35. A third section is a second border 28, 38 adjacent to a second edge 26 of the segment. The second border 28, 38 extends along the second edge 26 of the segment from the first set of perforations 15 to the second set of perforations 25. Both the first border 22, 32 and the second border 28, 38 have a material with reflective properties. The reflective properties of the border material enable the borders to emit a light in a visible wavelength when exposed to light. Accordingly, the reflective properties of the border material enable the border sections of the tape to become reflect a visible light with exposed to a light emitting source.

Between the first border 22 and the second border 28 is a middle section 40. The middle section is made of a material having a light color. In addition, the middle section 40 may be comprised of a material adapted to receive indicia from a writing utensil. This enables a person to write a message, an instruction, or any type of information in the middle section 40 of the segment 20. The indicia receiving material may be nylon, or a comparable material that is adapted to receive the indicia thereon. The person using the tape can use any type of writing material and write a message on the middle section. Accordingly, the middle section of the segment is adapted to convey information thereon.

Figure 2:
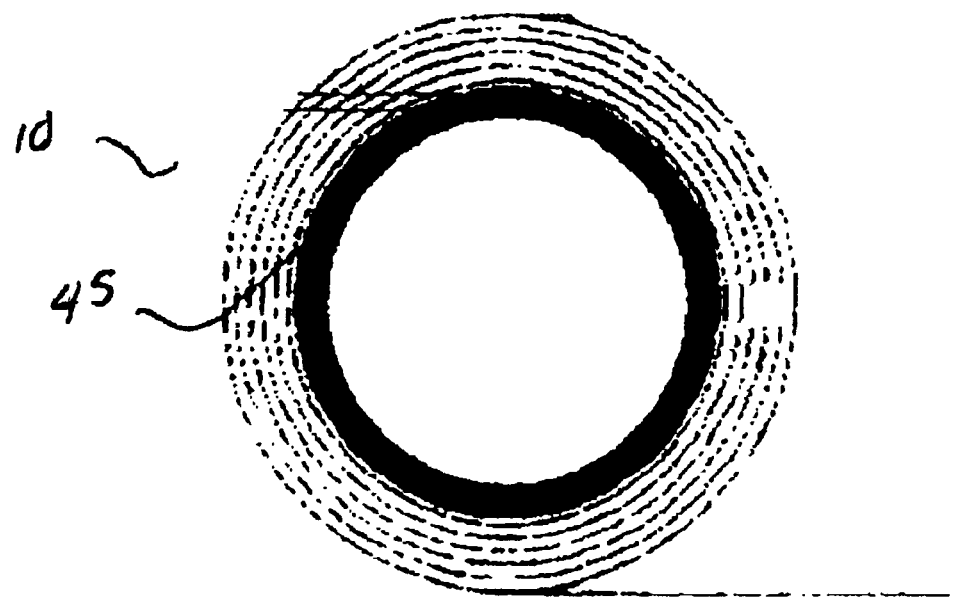
FIG. 2 is side view of a roll of the tape.

FIG. 2 is a side view of the tape in a rolled configuration. The tape is comprised of a plurality of segments wrapped around in inner core 45. Each adjacent segment 20, 30 is detachably secured to an adjacent segment by means of perforations 15, 25, 35. During use, an operator can merely detach the outermost segment from the roll 48 along a set of perforations 25, 35 and place it on an object or a person. The operator may detach an individual segment, or if the operator needs a longer piece of tape, they can detach the tape along a different set of perforations. In addition, the operator can write information on the middle section 40 either prior to detaching the segment(s) from the roll, or subsequent to the detachment from the roll. Similarly, the operator may use the tape as identifying marker without placing any indicia in the middle section. Accordingly, the tape provides a means for conveying information in the form of indicia placed on the middle section of the segment, or as a marker for emitting a reflective light of the border segment when exposed to a visible light.

Advantages Over the Prior Art

The tape shown in FIGS. 1 and 2 are an inexpensive and efficient means of conveying patient information in a trauma environment. The tape does not include any bandage thereon and therefore does not require any sterility. In addition, the reflective properties of the borders enables the tape to be used in low light environments. When light is in the vicinity of the tape, the border will reflect light in a visible wavelength. The tape may use an adhesive that enables it to be removed from the roll and attached to a secondary article, such as clothing, human skin, plastics, etc. The tape may initially be attached to a first secondary article, removed from that article, and reattached to a second secondary article. This enables the same tape to be used more than once if necessary. Accordingly, the tape is a non-sterile means of applying an identifier or identifying information with a reflective material that enables the tape to become visible in a low light environment.

Alternative Embodiments

It will be appreciated that, although specific embodiments of the invention have been described herein for purposes of illustration, various modifications may be made without departing from the spirit and scope of the invention. In particular, an exterior surface of the tape may include a waterproof material that is adapted to receive ink from a writing utensil. Since the tape is adapted to be used in different environments, the waterproof material will prevent the indicia on the middle section of the tape from washing off. In addition, the reflective material may be comprised of a plurality of colors that contain the reflective properties to enable the borders to reflect light in a visible wavelength. Different colors for the reflective material may be used to convey categoric information. The reflective material should not be limited to placement along a border region of a segment of the tape. Rather, the tape segments may be reconfigured to have the reflective material placed along an alternative region of the segment. Similarly, the middle region adapted to receive indicia from a writing utensil may be placed along an alternative region of the segment. The waterproof material adapted to cover the indicia receiving material may also be placed over the reflective material. Finally, the tape may be configured without perforations between adjacent segments. In a static position, the tape is placed on a roll prior to use. A person needing to utilize the tape must pull the tape from the roll, similar to the use of masking tape, and tear the tape from the roll at a desired position. This removes the requirement to place perforations on the roll, and enables the tape to be manufactured at a thickness that enables tearing from the roll without the use of perforations, scissors, or a similar cutting instruments. Accordingly, the scope of protection of this invention is limited only by the following claims and their equivalents.

We claim:

1. An apparatus for conveying information in an emergency, comprising:
   a) tape having a front side and a backside;
   b) said front side of said tape having a first section with a light reflective material placed along the exterior edge of said tape, and a second section with a material adapted to receive indicia from a writing utensil; and
   c) said backside of said tape having an adhesive.

2. The apparatus of claim 1, wherein said front side of said tape includes a waterproof material.

3. The apparatus of claim 1, wherein said tape includes a perforation at intervals along a length of said tape.

4. The apparatus of claim 3, wherein said tape is packaged in the in the form of a roll.

5. The apparatus of claim 4, wherein a segment of said tape is adapted to be removed from said roll along said perforation.

6. The apparatus of claim 1, wherein said second section of said front side of said tape is adjacent to said light reflective material.

7. The apparatus of claim 1, wherein said light reflective material may include a variety of colors.

8. The apparatus of claim 7, wherein said color is adapted to convey categoric information.

9. A method for conveying information in an emergency comprising the steps of:

a) packaging a length of tape with light reflective material placed along the exterior edge of said tape on front side of said tape, said length of said tape includes a plurality of segments joined together at preformed perforations;

b) applying indicia to a section of said front side of said tape adapted to receive indicia from a writing utensil;

c) removing a segment of said tape from another segment along said perforation; and d) adhering said removed segment of said tape removed from said length of tape to a secondary surface.

10. The method of claim 9, wherein said front side of said tape includes a waterproof material.

11. The method of claim 9, further comprising placing said light reflective material adjacent to said section adapted to receive indicia.

12. An apparatus for conveying information, comprising:

a) a material divided into a plurality of segments with each segment having a front side and a back side;

b) said front side of said material having a first section with a light reflective property along its exterior edge, and a second section with a material adapted to receive indicia from a writing utensil;

c) a waterproof material adapted to cover said second section; and d) said backside of said material having an adhesive.

13. The apparatus of claim 12, further comprising perforations between adjacent segments.

* * * * *